(12) United States Patent
Probert et al.

(10) Patent No.: US 7,306,953 B2
(45) Date of Patent: Dec. 11, 2007

(54) DETECTION OF DISEASE BY ANALYSIS OF EMISSIONS

(75) Inventors: Christopher Simon J. Probert, Bristol (GB); Norman Mark Ratcliffe, Bristol (GB)

(73) Assignee: The University of the West of England, Bristol, Bristol (GB)

( * ) Notice: Subject to any disclaimer, the term of this patent is extended or adjusted under 35 U.S.C. 154(b) by 0 days.

(21) Appl. No.: 11/036,206

(22) Filed: Jan. 14, 2005

(65) Prior Publication Data

US 2006/0008918 A1 Jan. 12, 2006

Related U.S. Application Data

(63) Continuation of application No. PCT/GB03/03246, filed on Jul. 18, 2003.

(30) Foreign Application Priority Data

Jul. 18, 2002 (GB) ................. 0216650.2

(51) Int. Cl.
*G01N 1/22* (2006.01)
*G01N 33/00* (2006.01)

(52) U.S. Cl. ............... 436/181; 436/63; 436/173; 436/161; 436/106

(58) Field of Classification Search .......... 436/63, 436/181, 173, 161, 106
See application file for complete search history.

(56) References Cited

U.S. PATENT DOCUMENTS

| | | | |
|---|---|---|---|
| 5,985,914 A * | 11/1999 | Zeldis et al. ............... | 514/455 |
| 6,057,162 A | 5/2000 | Rounbehler et al. | |
| 6,190,858 B1 | 2/2001 | Persaud et al. | |
| 6,221,026 B1 | 4/2001 | Phillips | |
| 2002/0017125 A1 | 2/2002 | Lewis et al. | |
| 2002/0090667 A1 * | 7/2002 | Ratcliffe et al. ............... | 435/34 |
| 2002/0182746 A1 * | 12/2002 | Mester et al. ............... | 436/178 |
| 2003/0235559 A1 * | 12/2003 | Sobol et al. ............... | 424/93.4 |
| 2005/0065446 A1 * | 3/2005 | Talton ............... | 600/529 |

FOREIGN PATENT DOCUMENTS

| | | |
|---|---|---|
| WO | WO 97/37587 | 10/1997 |
| WO | WO 98/41153 | 9/1998 |
| WO | WO 98/57145 | 12/1998 |
| WO | WO 00/12995 | 3/2000 |
| WO | WO 00/20852 | 4/2000 |
| WO | WO 00/32091 | 6/2000 |
| WO | WO 00/57182 | 9/2000 |
| WO | WO 00/61002 | 10/2000 |

OTHER PUBLICATIONS

Doguchi et al. (abstract). Ishikawa-ken Kogyo Shikenjo Kenkyu Hokoku, 2000, vol. 49, pp. 5-10.*
Suarez et al. (abstract) Gastroenterology, vol. 114, No. 5, May 1998, pp. 923-929.*
Gianfrilli, P. et al. Journal of Clinical Pathology, vol. 38(6), 1985, pp. 690-693.*
Fujita, K., et al., "Physicochemical Characteristics and Flora of Diarrhoeal and Recovery Faeces in Children with Acute Gastroenteritis in Kenya," *Annals of Tropical Paediatrics*, 10:339-345.
Vernia, P., et al., "Organic Anions and the Diarrhea of Inflammatory Bowel Disease," (1988) *Digestive Diseases and Sciences*, 33(11):1353-1358.
Mortensen, P. Brøbech, et al., "Short-Chain Fatty Acids in the Human Colon: Relation to Gastrointestinal Health and Disease," (1996) *Scand J Gastroenterol*, 31 Suppl. 216:132-148.

* cited by examiner

*Primary Examiner*—Maureen M. Wallenhorst
(74) *Attorney, Agent, or Firm*—Bret E. Field; Bozicevic, Field & Francis LLP (57) ABSTRACT

A method of determining the cause of disease is described, which method uses the detection of "signature" or "fingerprint" volatile compounds in an emission, especially flatus, from a patient.

38 Claims, 3 Drawing Sheets

FIG. 2

DETECTION OF DISEASE BY ANALYSIS OF EMISSIONS

CROSS-REFERENCE TO RELATED APPLICATIONS

This application claims priority to the filing date of the PCT Patent Application Ser. No. PCT/GB/2003/003246 filed Jul. 18, 2003; which application claims priority to GB Patent Application Serial No. 0216650.2 filed on Jul. 18, 2002; the disclosures of which are herein incorporated by reference.

INTRODUCTION

1. Field of the Invention

This invention relates to the detection of disease by the analysis of emissions. More particularly, the present invention relates to a non-invasive method of diagnosis by the analysis of fluid emissions from the human or animal body for the presence of compounds indicative of a disease state.

2. Background of the Invention

It is well known that certain volatile compounds can be detected on the breath and that such volatiles can be indicative or diagnostic of certain diseases or conditions. For example, it has long been recognised that the smell of acetone on the breath is indicative of ketosis, and that this can be related to diabetes mellitus.

It is also well known that alcohol on the breath is indicative of blood alcohol levels and that the so-called Breathalyser can be used to determine blood alcohol levels. Initially, breath alcohol determination relied on a colour change when a subject exhaled slowly over potassium dichromate crystals. More recently, for alcohol detection, exhaled breath has been analysed electronically.

Similarly, it has previously been recognised that flatus gas associated with certain disease conditions is malodorous, and may often have a characteristic odour in a manner similar to that described above for ketosis. For example, nurses have found that particular odours, such as, "sweet" or "acrid" odours, may generally be associated with particular diseases. It has been postulated that such odours may arise from the presence of cellular metabolites in the flatus which are different from the metabolites of the normal or healthy lower gut or bowel. It has also been postulated that the gases from eructation can be indicative of gastric conditions, such as gastric ulcers or *helicobacter* infection.

One area where such information would be extremely useful is in the diagnosis of bowel diseases, especially those which are associated with diarrhoea. Moreover, the ability to rapidly diagnose whether diarrhoea was caused by the presence of micro-organisms or parasitic infestation, an acute condition, or by a gastrointestinal disease, or a bowel disease or condition, which is likely to be chronic, would be particularly useful. Similarly, the ability to detect lung infections non-invasively could prove useful in differentiating between acute infections and chronic diseases and infections.

SUMMARY OF THE INVENTION

In the description which follows, the present invention will be described with particular reference to its preferred application in the analysis of flatus gas or gas evolved from a stool sample, however it is not intended that the present invention be limited thereto since it finds equal utility in its application to other fluid emissions from the human body such as exhaled air or eructation.

Diarrhoea due to infection is a major cause of morbidity and mortality. In the United States alone, 3 million patients suffer from *Clostridium difficile* associated diarrhoea and colitis (CDAD) each year (Mylonakis E, Ryan E T, Calderwood S B. *Clostridium difficile*-associated diarrhoea—a review. Arch Int Med 2001; 161:525-533). In 1989, it was reported that 10% of patients hospitalised for more than 2 days suffer from CDAD (McFarland L V, Nulligan M E, Kwol R Y, Stamm W E. Nosocomial acquisition of *Clostridium difficile* infection. N Engl J Med 1989; 26:204-10). In England and Wales, there are approximately 15,000 cases of *Clostridium difficile* per annum, but this is dwarfed by the 55,000 cases of *Campylobacter* infection. However, viral infections of the gastrointestinal tract are also a major problem: in England and Wales, there are 16,000 cases of Rotavirus infection per annum (as reported, 2002) and in the United States Rotavirus infection accounts for 56,000 hospitalisations per year and 48% of viral gastroenteritis in the US (Lew J F et al. 6-year retrospective surveillance of gastroenteritis viruses at 10 emergency medical centres in United States and Canada. Pediatr Infect Dis J 1990; 9:709-14). In developing countries Rotavirus accounts for 600,000 deaths per year (Ciariet M, Estes M K. Interactions between Rotavirus and gastrointestinal cells. Curr. Opinion Microbiol 2001; 4:435-41.). Whilst there remain few appropriate anti-viral agents for these disorders, isolation of infected individuals may limit epidemics.

Despite the development of ELISAs and molecular techniques, in most cases there is a delay of several days between the collection of a stool sample and diagnosis. The delay is in part due to shipping of the samples to an appropriate laboratory, but mainly due to time required to complete the diagnostic techniques in common use. The limited availability of rapid microbiological or parasitological techniques in developing countries, generally due to their expense, compounds the problem. In some epidemics, stool samples have been flown to the United States for microbiological or parasitological processing. Depending on the patient's circumstance, the results of a diagnostic delay may range from lost productivity, to prolonged hospitalisation or even death. There is a pressing need to make a rapid, accurate diagnosis in all patients.

Diarrhoea has a wide variety of physical characteristics that have been used to try to determine its aetiology. The term "flatology" was coined to describe the association between characteristic flatus odours and specific diseases. The flatus that accompanies diarrhoea can be particularly unpleasant both for the patients and for those attempting to care for them, however the characteristics of the flatus have received very little academic interest. Indeed, very little interest has been shown in flatology for 20 years (Levitt M. D. Intestinal gas production-recent advances in flatology. N Engl J Med 1980; 302:1474-1475).

The present inventors, contrary to this teaching, have continued in this field and have taken a novel approach to the analysis of flatus to determine whether any volatile compounds can be found which may be used to identify the cause of the diarrhoea and importantly to eliminate infection or infestation as the cause of diarrhoea in the detection of diseases of the bowel or the lower intestine.

The compounds responsible for the odour of flatus arise from cell metabolism and are referred to as volatiles or volatile organic compounds (VOCs). The volatile cellular metabolites may be in gaseous form or may be present dissolved in moisture vapour/droplets in the emission. While the majority of volatile compounds are likely to be organic it is wholly possible that inorganic compounds such as nitrogen- or sulphur-compounds may also be present, and it is not intended to exclude such compounds from the scope of the present invention. The present inventors studied flatus from patients with diarrhoea and from healthy volunteers. It was found that characteristic volatiles could in fact be associated with infection or infestation by individual microorganism or parasite species or from altered metabolism in a gastrointestinal disease state such as by aberrant metabolism of cells.

Gastrointestinal disease states of interest for the present invention include endocrine or exocrine disorders, such as chronic pancreatitis, inflammatory bowel diseases, such as Crohn's disease or ulcerative colitis, irritable bowel syndrome, coeliac disease, gastroenteritis, bacterial overgrowth in the intestines, food intolerance and cancers. This list in not intended to be limiting and the present invention finds equal utility is distinguishing many other diseases of the gastrointestinal tract (GI diseases) from those due to infection or to parasitic infestation, for example by protozoa or worms.

Infection may be bacterial, for example infection with *Clostridium difficile*, viral, for example rotavirus, or fungal, for example with *Candida*. Parasites which infest the GI tract include *Giardia lamblia, Cryptospiridium* spp, *Leishmania* spp, *Schistosoma* spp (Bilharzia), *Onchocerca* and *Ioia* (filariasis), amoeba, tapeworms, roundworms and thread worms. Again, this list is not intended to be limiting as many other organisms may infect the GI tract.

Colorectal cancer (CRC) is the second most common cause of cancer death in the UK (Cairns S, Scholefield J H). 30,000 people are affected each year with an average 5-year survival rate of 40%. 80% of patients present with invasive or metastatic cancer. Screening has been advocated but the imposition of the so-called two-week rule means that the pressure on hospitals to deal with suspected cancers is great, displacing invasive screening with sigmoidoscopy or colonoscopy. Faecal occult blood testing has been advocated but it has poor sensitivity (30% with single tests and 92% with annual testing). The present inventors' approach would have to compete with this.

In assessing volatiles in gas evolved from faeces of patients with CRC, the present inventors have explored the probability that the cancer produces unique chemicals and/or interacts with bacteria in a unique manner to generate specific volatiles. It is well know that the mucins associated with CRC differ from normal and that bacteria metabolise mucins (Corfield A P et al, Sylvester P A et al, Pant K D et al). It is suggested that the bacterial flora is different amongst patients with CRC (Moore W E, Moore L E). Inflammatory bowel disease, Crohn's disease and ulcerative colitis, have a prevalence of 70 and 100 cases/100,000, respectively (Probert C S J et al) and thus affect nearly 100,000 patients in the UK. Typically these disorders cause diarrhoea, but separating them from the numerous patients who suffer from irritable bowel syndrome can be complicated. However, there is anecdotal evidence, from patients and clinicians, that the flatus from patients with active inflammatory bowel disease has an unusual, possibly specific, odour.

The term "gastrointestinal tract" as used herein is intended to take the broad definition used in this field which includes both the alimentary canal and other organs involved in the digestion of food such as the salivary glands, the pancreas, the gall bladder and the liver or any other organ which forms a part of the digestive system, since altered metabolism in any one of these areas may result in diarrhoea.

It is therefore an object of the present invention to provide a non-invasive method of diagnosis to ascertain the causative agent of diarrhoea.

Accordingly, the present invention provides a method of analysing emissions from the human or animal body, the method comprising the steps of collecting a sample of emission from a patient, and analysing the emission for the presence of volatile compounds indicative of the presence of disease.

Advantageously, the method of the present invention provides a rapid indication of the presence of pathogens as opposed to innocuous or normally resident organisms.

Preferably, the emission is a gaseous emission, for example, exhaled air, eructation or flatus. However, other emission samples such as ascites, sputum, urine, faeces, blood or tissue may be used. In this manner volatiles contained in microbiological metabolites produced by micro-organisms in the sample may be used to detect the presence of pathogens. In the most preferred embodiment the emission is flatus or gas evolved from a stool sample. Where the gas is evolved from stool, it is preferable that the gas is evolved at ambient temperature and it is especially preferred that the gas is the gas contained in the headspace of the collection vessel.

Collection of the gas may be done in many ways, for example by emission of the gas directly into a collection chamber and/or an associated vessel, by catheterisation of the area of interest, the gas then being analysed by typical gas analysis methods, for example, gas chromatography and/or mass spectrommetry. These collection methods are prone to leakage leading to loss of sample. In the preferred application of the analysis of flatus gas, it is especially difficult to collect the flatus without loss of sample. It is therefore another object of the present invention to provide a sample collecting device which allows easier collection and reduces the amount of sample lost.

The present invention therefore also includes gas collection means for use in the method of the present invention. Preferably, the gas collection means are in the form of a solid sorbent, such as a thin film of a sorbent polymer, for example polydimethylsiloxane on a fibre or a more conventional sorbent such as Tenax may be employed. The sorbent may be absorbent or adsorbent.

The sorbent may be used in combination with a membrane offering differing permeabilities to give selectivity to certain vapours or so-called smart membranes may be used that is, materials capable of selectivity and/or with the ability to change permeability based on either polarity change or pore size or both. Typically the sorbent is capable of multiple usage, all sorbed gases having been desorbed by heating to a high temperature. However a disposable fibre may be used, the fibre being brought into close proximity with the stool or even being dipped into the stool, followed by thermal desorption of flatus volatiles directly or indirectly from the stool sample. The disposable fibre in practice could be heated to one temperature and maintained at that temperature to cause evolution of all flatus volatiles, on a temperature ramp or a series of steps in temperature employed to cause fractionation of the volatiles. This latter approach could simplify analyses of the gas mixture.

Thermal desorption may typically be used to release the gases from the absorbent or adsorbent material for analysis.

Preferably, the sample is analysed by mass spectroscopy, gas chromatography or by use of a so-called electronic nose—an electrochemical sensor, or an array of sensors, which specifically detects volatile compounds, especially pre-selected volatile compounds or patterns of volatile compounds. The use of a single sensor targeted to one marker compound or volatile would also be a suitable method for some analyses, for example Rotavirus.

An array of such sensors with appropriate pattern recognition software would then give a rapid diagnosis. In the case of potato tuber diseases, it has previously been shown (De Lacy Costello, B. P. J., Ewen, R. J., Gunson, H. E., Ratcliffe N. M. & Spencer-Phillips, P. T. N. The development of a sensor system for the early detection of soft rot in stored potato tubers. *Measurement Science and Technology.* 11, 1685-1691 (2000). De Lacy Costello, B. P. J., Evans, P., Ewen, R. J., Gunson, H. E., Ratcliffe N. M. & Spencer-Phillips, P. T. N. GC-MS analyses of volatile organic compounds from potato tubers inoculated with *Phytophthora infestans* or *Fusarium coeruleum. Plant Pathology* 50, 489-496 (2001)), that the strategy of gas chromatography/mass spectroscopy vapor analysis followed by sensor development to produce a minimal array of sensors is a successful strategy in the design of relatively inexpensive electronic nose instrumentation. This means that near patient testing will be possible permitting an economic diagnosis to be made within minutes of the flatus being collected.

The volatile compounds preferably form at least a part of a "fingerprint" or "signature" pattern during chemical analysis for a particular micro-organism. For example, the present inventors have found that the presence of furans in flatus is indicative of infection with *Clostridium difficile*, that ammonia is indicative of Small round-structured virus-2 (also known as Norwalk virus), astrovirus or adenovirus, that ethyl dodecanoate is indicative of Rotavirus. Interestingly, *Campylobacter* infection produces similar volatiles to those found in normal patients, however, it was also found that patients with *Campylobacter* infection produced no flatus containing volatiles of the terpene/hydrocarbon type. Infection with *Giardia lamblia* contains volatiles associated with high fat content due to the high fat content in stool-samples of patients affected with this organism. Hence, examples of the pre-selected volatile compounds include furans, ammonia, amines, acids, esters, ethers, alcohols, sulfides, sulphates, thiols, aldehydes, ketones, alkanes, alkenes, terpenes, phenols, indoles, nitrates, aromatic compounds, hydrocarbons and sugars.

The present inventors have shown that the composition of volatiles in the flatus from normal subjects is remarkably similar, however in patients with various types of diarrhoea the distribution of volatiles is different and that characteristic changes occur with specific types of diarrhoea. Without wishing to be bound by theory, the present inventors have postulated that volatiles present in stool samples are also present in flatus, since flatus is simply gas evolved from the faeces while still in the gut. In the experiments described herein, in order to obtain larger quantities of gas, gases evolved from stool samples were analysed rather than flatus per se due to problems currently encountered with the non-invasive collection of flatus.

These experiments showed that indoles are ubiquitous in normal stool and in most patients with diarrhoea and hence in flatus. Their occurrence is related to the metabolism of tryptophan by *Escherichia coli*. Indeed a simple laboratory test for *E. coli* based on the detection of indoles has been in clinical use since 1963 (Vracko R and J C Sherris, Indole-spot-test in bacteriology. Am J Clin Path 1963; 39:429-32). Board spectrum antibiotics suppress the growth of *E. coli* allowing the overgrowth of *C. difficile* which does not produce indole. The reduced production or absence of indoles in patients with *C. difficile* infection is likely to be a result of the disruption of metabolism by *E. coli*, however the presence of large amounts of furans, which are not prevalent in flatus from normal faeces, is harder to explain. Furans are likely to be related to bacterial metabolism of furanose.

Many *Clostridia* species are capable of fermenting sugars and amino acids. Efforts were made to rapidly identify *C. difficile* in cultures by presence of p-cresol and caproic acid (Johnson L L, McFarland L V, Dearing P, Raisys V, Schoenknecht F D. Identification of *Clostridium difficile* in stool specimens by culture-enhanced gas-liquid chromatography. J Clin Microbiol 1989; 27:2218-21. Nonhoff C, Struelens M J, Serruys E. Evaluation of gas-liquid chromatography (GLC) for rapid detection of *Clostridium difficle* in faecal specimens. Acta Clinica Belgica 1995; 50:76-80). However, this approach was not widely used and, unlike the present inventors' approach, requires the organism to be cultured before it can be identified. Multiple enzyme immunoassays do provide a rapid test for *C. difficile* (Delmée M. Laboratory diagnosis of *Clostridium difficile* disease. Clin Microbiol Infection 2001; 7:411-37). However, ELISAs have a sensitivity of 70-90% and specificity of 99% (Gerding D N, Johnson S, Peterson L R, Mulligan M E, Silva. *Clostridium difficile*—associated diarrhoea and colitis. Infect Control Hosp Epidemiol 1995; 16:459-77). As quick as they may be, they are not used for near-patient-testing and still are dependent on transport to a microbiology laboratory.

Rotavirus is the most common cause of viral gastroenteritis, however small round-structured viruses, astrovirus and adenoviruses account for at least 2,000 reported cases each year in England and Wales (Public Health Laboratory Services figures). Each of these enteric viruses infects the small intestine, so it is not surprising that the flatus associated with them share some chemical characteristics. Ammonia was found in the flatus patients with these viruses. However, Rotavirus is exclusively associated with ethyl dodecanoate. Dodecanoic acid may also be a marker compound as it is absent from normal stool but is present in stools from patients with Rotavirus. The source of these VOCs has not been determined.

*Giardia lambia* infects both the large and the small intestine. The presence of ammonia in one of the patients with *Giardia lamblia* supports the finding that small intestinal infection is associated with flatus that contains ammonia. However, the amount of small intestinal histological change that is evident amongst patients with giardiasis is quite varied, so it is conceivable that the presence of ammonia is also determined by the amount of mucosal damage.

A relative increase in propionic and butyric acids have been reported in the stool of patients with Rotavirus (Brooks J B. Review of frequency-pulsed electron-capture gas-liquid chromatography studies of diarrhoeal disease caused by members of the family Enterobacteriaceae, *Clostridium difficile* and Rotavirus J Clin Micriobiol 1986; 24:687-91). The present inventors found that, while the amount of short chain (C3-C5) fatty acids appeared greatest in the flatus of patients with Rotavirus, there were also significant amounts in patients with *campylobacter* and *clostridium difficile*.

The finding of absent hydrocarbons and terpenes in *campylobacter* spp. remains to be explained.

These chemical fingerprints could be used to rapidly determine the aetiology of the diarrhoea in any setting. However, the need is often most urgent in the immunocompromised patient—the bone marrow recipient, the HIV/

AIDs patient as well as the very young or old. For example, such patients often suffer from diarrhoea while taking dietetic supplements such as those which are prepackaged, known as carton foods. Often in such patients no infectious agent is identified as the source of the diarrhoea. The present inventors (among others) have postulated that this may be due to osmotic drag or other impedance of water absorption by the colon, due to the presence of partially digested or modified sugar components, or degradation products (for example, acid hydrolysis in the stomach) of the synthetic sugars used in these foods. The present invention therefore provides a method which allows a rapid diagnosis to eliminate infection as the cause of such diarrhoea. Additionally, the present inventors have obtained preliminary data which suggests the identity of these synthetic sugar derivatives.

Optionally, especially where the emission to be analysed is gas evolved form stool, the present invention includes a pre-treatment step in order to modify or enhance the vapour profile of the volatiles contained therein. For example, the stool sample may be made more alkaline in order to enhance amine evolution. Alternatively, a stool sample may be heated to accelerate or improve the emission of gas and hence the volatiles contained therein.

Additionally, it should be noted that as part of a full diagnosis, standard assessments of stool sample, for example colour, viscosity, pH, occult blood or fat microscopy may still be conducted.

BRIEF DESCRIPTION OF THE FIGURES

FIG. 1 shows a gas chromatograph profiles for (1a) normal patients: Peak A Dimethyl Disulphide, Peak B Benzaldehyde, Peak D 4-Methyl Phenol, Peak E Indole, Peak F 3-Methylindole, and for patients infected with (1b) *Clostridium difficile*: Peak A Acetic Acid, Peak B Butanoic Acid, Peak C 2-Furancarboxal dehyde, Peak D 5-Methyl-2-Furancarboxaldehyde, Peak E Methyl Furancarboxylate, Peak F 2-Hydroxy Benzaldehyde, Peak G 4-Methyl Phenol, Peak H 2-Methoxy Phenol.

DESCRIPTION OF SPECIFIC EMBODIMENTS

The present invention will now be described in more detail, by way of example only, with reference to and as illustrated by the accompanying drawings of which.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

Flatus was obtained from stool samples from 38 subjects with diarrhoea and from 6 healthy controls. For each subjects, the aetiology of the diarrhoea was determined by routine microbiological assessment (n=35). Three of the subjects had an exacerbation of inflammatory bowel disease involving the colon. Diarrhoea (ca 0.5 ml) and semi-solid excrement (ca 0.25 g) samples were portioned in sealed headspace vials (Supelco, 10 ml) designed for solid phase microextraction (SPME). Samples were equilibrated in a water bath (37° C.) and their volatile compounds entrained from the headspace on to SPME fibre (Supelco, 85 µm Carboxen/poiydimethylsiloxane, 12 hrs). Any samples not extracted within 1 hour of collection were stored in the vials at −18° C. Sample volatile compounds were desorbed from the fibre thermally via splitless injection (HP 5890 II, 1.5 mins, 250° C.) onto a thick film column (Supelco, SPB-1 Sulfur, 30M×0.32 mm β 20). Volatile compounds were eluted from the column (35° C. (5 mins)×10° C./min −250° C. (2 mins), 1 ml/min) directly into a mass spectrometer (HP 5971) full scan (positive mode, 15-60 amu 2 mins, 19-350 amu until 28.5 mins). Compounds were identified by the mass spectral library match (NBS) and by their elution order. The estimated limit of detection was about 10 ng/ml.

Volatiles were concentrated using solid absorbance media and analysed by a combination of gas chromatography and mass spectroscopy. As expected, the chromatographs revealed an enormous number of VOCs, many of which were shared by both normal subjects and patients with diarrhoea. Indeed, although there are apparent differences in the smell of normal flatus due to the complexity of the diet, most of the VOCs compounds are shared. However, when the present inventors scrutinised the chromatographs from patients with infectious diarrhoea the pattern was different.

Some conditions were associated with the generation of VOCs not found in normal flatus, while in others normal volatiles were absence.

Additionally, the present inventors have undertaken a pilot study of volatiles from stool samples from 16 patients with non-infectious diarrhoea. The volatile profiles were different from those from patients with infectious diarrhoea in several key respects. For instance, no ethyl dodecanoate was found in any of these samples; the only samples in which the present inventors have found this volatile remains from those from patients with Rotavirus. Similarly, the pattern of furans and indoles found in patients with *C. difficile* have not been found in any other sample.

However, there are other possible patterns emerging from the analysis of volatiles derived from stool samples from patients with non-infectious diarrhoea. For example, preliminary work has shown that hexanal may be indicative of chronic pancreatitis, although this has so far only been assessed in two patients. This result may have important significance since chronic pancreatitis is now difficult to diagnose reliably due to the difficulties encountered, at least in the UK, in obtaining the traditionally required faecal fat investigations. Additionally, work with Crohn's patients has shown that the propyl ester of propanoic acid may be indicative of this disease. It has been suggested that hydrogen appears to be linked to Irritable Bowel Syndrome (IBS) and the present methodology could be applied to using hydrogen as a marker or pre-selected volatile for IBS when using flatus or stool gas.

Normal Flatus

Figure 1A:
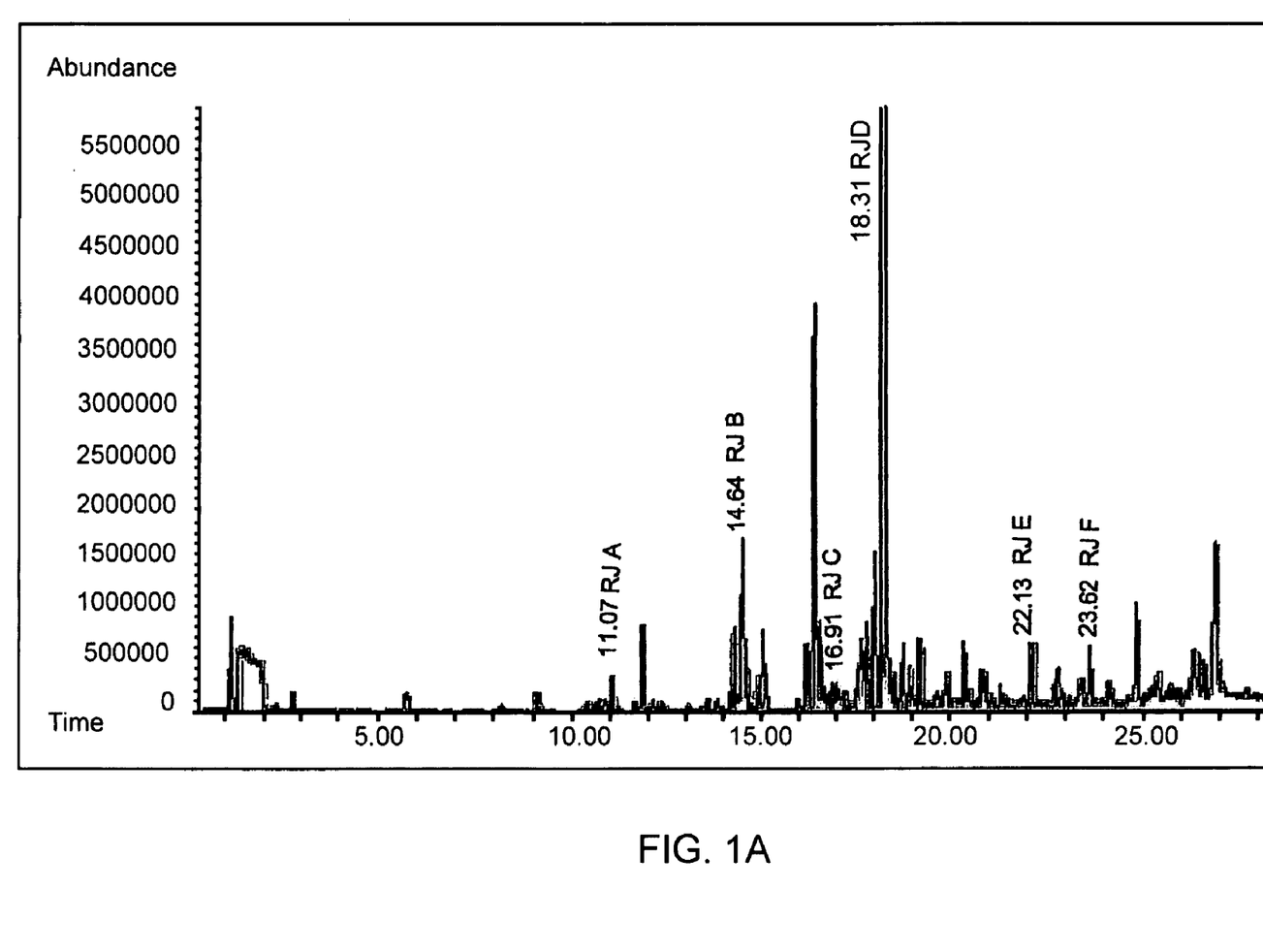

The volatiles present in the flatus of normal subjects (n=6) were remarkably similar. The predominant class of volatile was the phenols which accounted for 20-50% of the measured volatiles (see FIG. 1a). In each subject, 4-methyl phenol was the by far the most prevalent phenol. Indole and 3-methyl indole were also abundant (5-25%) in the flatus from normal subjects as were a group of volatiles the present inventors have called terpenes and hydrocarbons (10-20%). The principle volatile components of normal flatus were: 4-methyl phenol, indole, 3-methyl indole and limonene. Benzaldehyde was ubiquitous though less abundant.

*Clostridium Difficile*

Figure 1B:
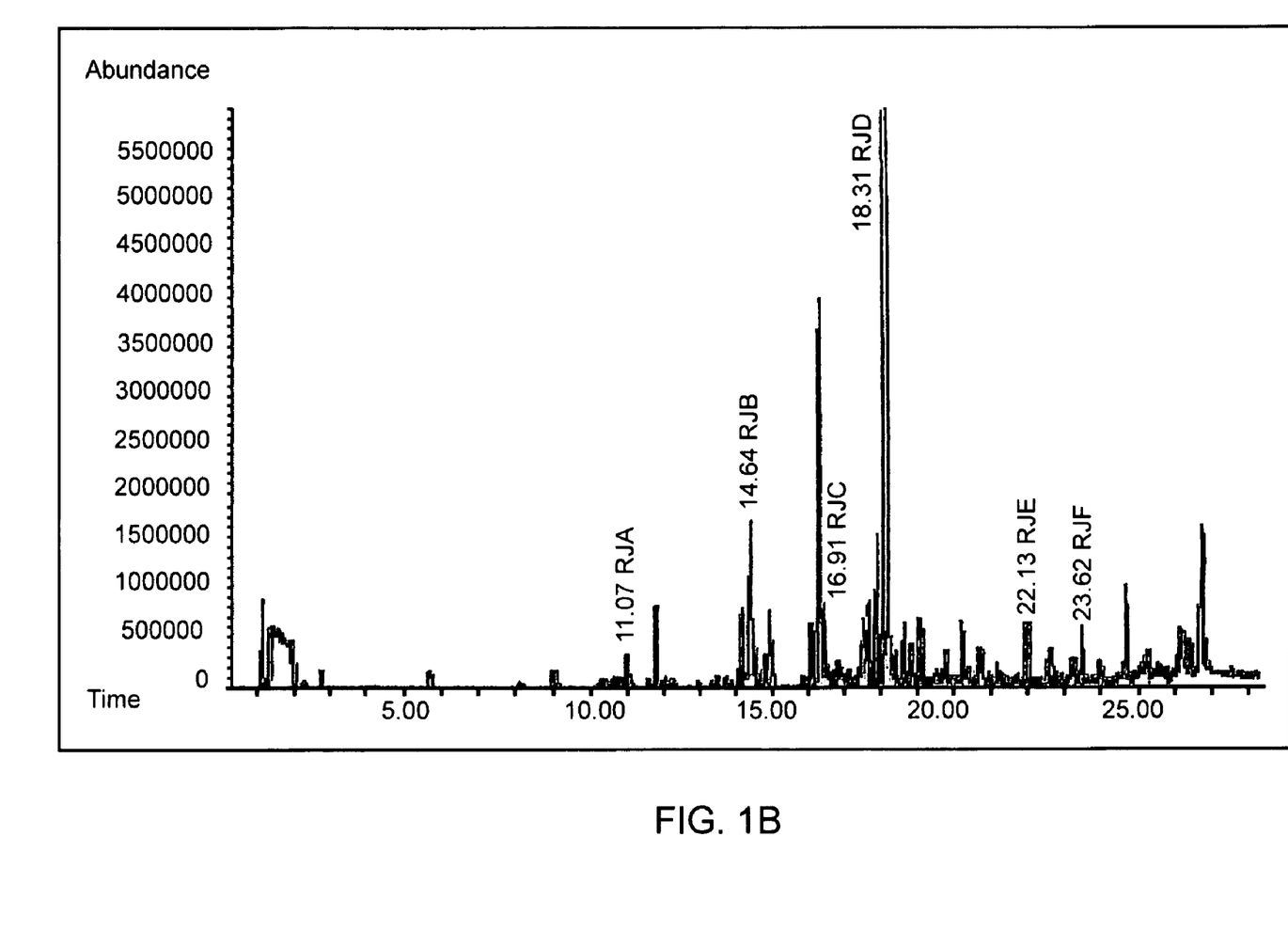
Figure 2:
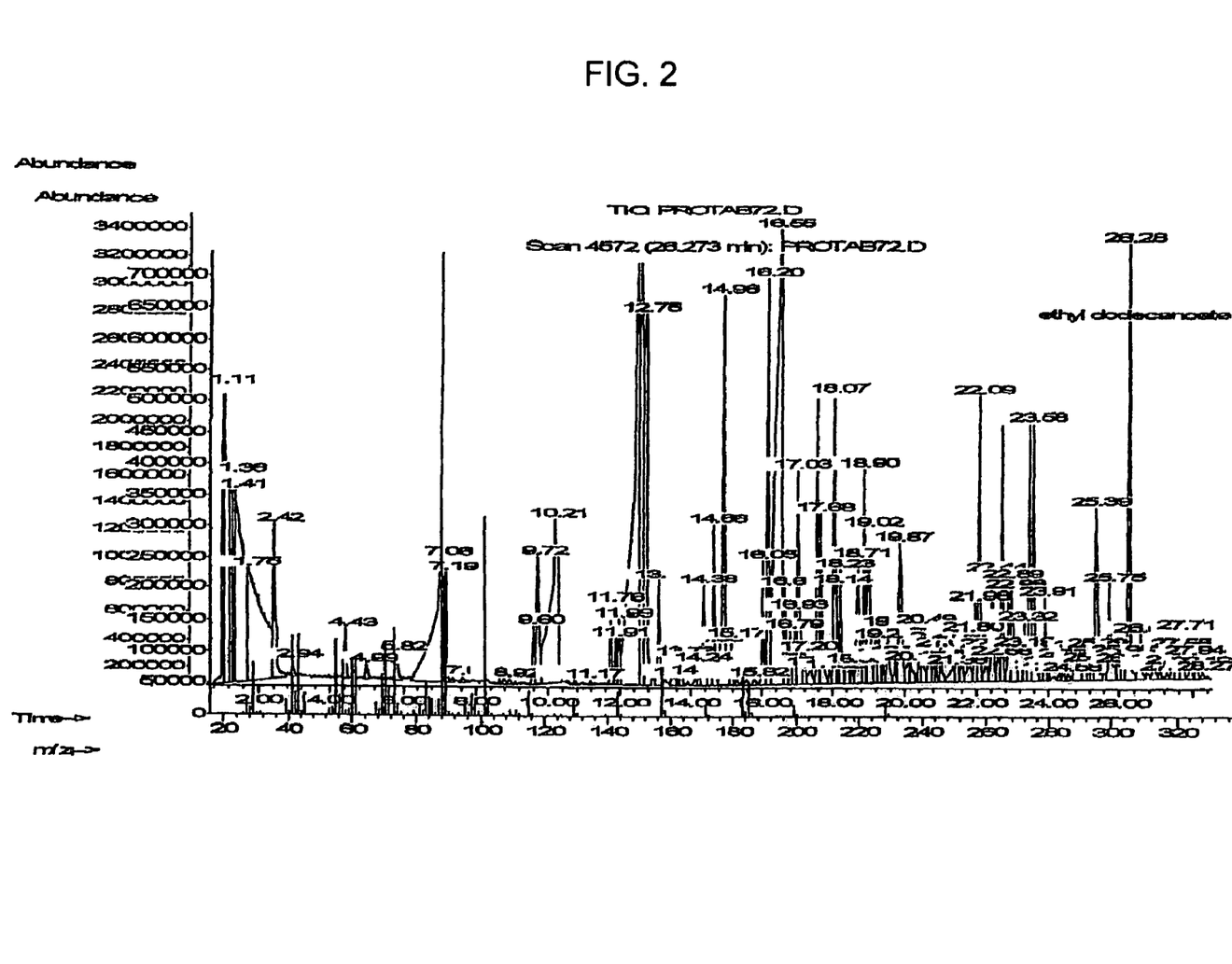
FIG. 2 shows gas chromatograph profiles a patient suffering from Rotavirus infection.

In flatus from patients (n=6) with diarrhoea due to *Clostridium difficile*, furans were particularly prevalent (25-55% of the measured volatiles). Furans are not found in the flatus of normal subjects nor that from the majority of patients with other forms of infectious diarrhoea. 2-furancarboxaldehyde and 5-methyl-2-furancarboxaldehyde (see FIG. 1b) were common in samples from patients (100% and 84% respectively) with *Clostridium difficile*, however both of these were found in a sample from one of the five patients suffering from *Campylobacter*. 2-furancarboxaldehyde was found in the flatus from patient with Adenovirus diarrhoea and in samples from four of the five patients with Rotavirus. Note that in stool flatus from a normal stool (FIG. 1a) there are peaks representing indoles, whilst in the patient with *Clostridium difficile* (FIG. 1b) indoles are absent but furans are prevalent.

Only one of the patients with *Clostridium difficile* had 3-methyl indole in their flatus. However, 3-methyl indole was present in flatus from all normal subjects and from most patients with diarrhoea. In particular, 3-methyl indole was found in both of the patients without *Clostridium difficile* who were found to have 2-furancarboxaldehyde in their flatus. Thus, the absence of 3-methyl indole in the presence of high levels of 2-furancarboxaldehyde occurred exclusively among patients with *Clostridium difficile*. However, even without quantification the presence of these furans, in the absence of 3-methyl indole may be used to diagnose *Clostridium difficile* (Table 1).

Rotavirus

The flatus from patients with Rotavirus (n=5) was characterized by the presence of ethyl dodecanoate. Only one of sample, from a patient with Adenoviral enteritis, contained this; the present inventors cannot exclude the possibility of dual pathology. Ethanol was also present in every sample from patients with Rotavirus, however ethanol was also present in the flatus from 2 of the 4 normal subjects. Dodecanoic acid may also be a marker compound for Rotavirus. It was present in 4 out of 5 patients with Rotavirus and absent in all other samples apart from one. Without wishing to be bound by theory it is possible that ethyl dodecanoate originates from later formation by reaction of ethanol with dodecanoic acid.

Small Round-Structured Virus/Astrovirus/Adenovirus

Eight patients with diarrhoea due to small round structured virus 2 (often called Norwalk virus) were studied. Ammonia was found in 7 of flatus samples from them, however the present inventors do not know whether all 8 subjects had the same strain of virus. Interestingly, ammonia was also found in both subjects with astrovirus, ⅔ with Adenovirus, ⅓ with Giardiasis and ⅕ with Rotavirus. However, as Rotavirus is exclusively associated with ethyl dodecanoate and normal stool are strongly associated with acetone (and are unlikely to sampled) is should be possible to use volatiles to diagnose patients with other viruses studied. Once again it is possible that routine EM studies may have missed dual infection.

*Giardia Lamblia*

Three samples of flatus from patients with giardiasis were studied. The stool of patients with this infection often looks abnormal and as a pale grey colour, probably due to its fat content. Despite the present inventors' suspicion that volatiles related to its fat content may be present, the present inventors were unable to find any characteristic changes in the volatiles in the flatus associated with this infection.

*Campylobacter*

Patients with *Campylobacter* (n=5) each produced flatus which was quite similar to normal stool. Phenols were abundant (10-40% of measured volatiles) as were indoles (20-30%), moreover patients with *Campylobacter* infection produced flatus containing more volatile organic acids (30-35% of measured volatiles) than any other group of patient. However, patients in this group produced flatus that contained no volatile compound belonging to the terpenes/hydrocarbon group. Every other sample analysed contained VOCs belonging to this group.

Coeliac Disease

The volatile profile of gas evolved from stool samples of newly diagnosed patients with coeliac disease contained no (or negligible amounts) of short chain organic acids or esters, which are abundant in virtually all the other samples studied (circa 70 samples). This absence of volatiles or other moieties detectable in normal stool samples is presumed to be indicative of coeliac disease by virtue of the altered metabolism of the bowel in this disease. One of the coeliac patient samples tested also showed the presence of hexanal. This may be indicative of the poor or mal-absorption of food present in this disease state.

Ulcerative Colitis

Samples of flatus/stool gas from patients suspected of suffering from ulcerative colitis were studied. Despite the small number of patients studied, octyl butanoate appears to be the most predictive of several possible marker compounds for this disease.

Crohn's Disease

Samples of flatus/stool gas from seven patients suffering from this disease were tested. Six of the samples showed the presence of the propyl ester of propanoic acid, which was not present in the samples from normal patients or in the samples from patients with infectious diarrhoea. It is presently believed that the presence of the propyl ester of propanoic acid (PEPA) may therefore be indicative of Crohn's disease, of the seven patients tested, PEPA was detected in 4, and was possibly detected in two.

Chronic Pancreatitis

Samples of flatus/stool gas analysed from two patients with chronic pancreatitis showed the presence of hexanal. This was not present in the normal samples tested. The presence of hexanal may result from the poor or malabsorption of fats associated with chronic pancreatitis. Hexanal may therefore be indicative of chronic pancreatitis, although the numbers of patients tested to date is very low, and the compound was also present in one of the samples from a Coeliac patient.

TABLE 1

Diagnostic Value of VOCs in Flatus of Patients With Infectious Diarrhoea

|  | Marker | $\chi^2$ | p | Sensitivity | Specificity | PPV | NPV |
|---|---|---|---|---|---|---|---|
| Clostridium difficile (I) | Indole negative | 6 | 0.01 | 50% | 89% | 43% | 92% |
| Clostridium difficile (ii) | 3MI negative | 5.2 | 0.02 | 83% | 66% | 28% | 96% |
| Clostridium difficile (iii) | 3MI negative 2FC positive | 28.7 | 8.6 E-8 | 83% | 97% | 83% | 97% |
| Clostridium difficile (iv) | 3MI negative 5M2FC positive | 27.9 | 1.3 E-7 | 67% | 100% | 100% | 95% |
| Campylobacter | No terpenes/ Hydrocarbons | 25.4 | 4.7 E-7 | 100% | 92% | 63% | 100% |
| Rotavirus | EDD positive | 35.7 | 2.3 E-9 | 100% | 97% | 83% | 100% |
| SRSV, Adeno-, Astro-virus (I) | Ammonia positive | 21 | 3.3 E-6 | 75% | 93% | 86% | 87% |
| SRSV, Adeno-, Astro-virus (ii) | Ammonia positive EDD negative | 25.6 | 4 E-7 | 75% | 93% | 86% | 87% |

The strength of association is shown using $\chi^2$ test, sensitivity and specificity, positive predictive value (PPV) and negative predictive values (NPV). 3MI: 3-methylindole, 2FC: 2-furancarboxaldehyde, 5M2FC: 5-methyl-2-furancarboxaldehyde, EDD: ethyl dodecanoate.

The invention claimed is:

1. A method of analysing fluid emissions from a body to diagnose a disease state in said body, the method comprising the steps of:
    collecting a sample of fluid emission from a body, and
    analysing the emission solely for the presence or absence of at least one predetermined volatile compound wherein the emission is flatus or gas evolved from stool, wherein the presence or absence of said predetermined volatile compound in said emission is indicative of a disease state, to determine the presence or absence of said disease state in said body.

2. A method according to claim 1, wherein the disease is a disease of the gastrointestinal tract.

3. A method according to claim 1, wherein the emission is collected non-invasively.

4. A method according to claim 3, wherein the emission is collected by use of a solid sorbent.

5. A method according to claim 4, wherein the solid sorbent is a polydimethylsiloxane-coated fibre, Tenax, or a smart membrane.

6. A method according to claim 5, wherein the emission is analysed at least one of mass spectroscopy, gas chromatography and electronic nose.

7. A method according to claim 5, wherein the emission is de-sorbed prior to analysis.

8. A method according to claim 5, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

9. A method according to claim 4, wherein the emission is analysed at least one of mass spectroscopy, gas chromatography and electronic nose.

10. A method according to claim 4, wherein the emission is de-sorbed prior to analysis.

11. A method according to claim 4, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

12. A method according to claim 3, wherein the emission is collected by use of a liquid sorbent.

13. A method according to claim 12, wherein the emission is analysed by at least one of mass spectroscopy, gas chromatography and electronic nose.

14. A method according to claim 12, wherein the emission is de-sorbed prior to analysis.

15. A method according to claim 12, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

16. A method according to claim 3, wherein the emission is analysed by at least one of mass spectroscopy, gas chromatography and electronic nose.

17. A method according to claim 3, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

18. A method according to claim 1, wherein the emission is analysed by at least one of mass spectroscopy, gas chromatography and an electronic nose.

19. A method according to claim 18, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

20. A method according to claim 1, wherein the emission is de-sorbed prior to analysis.

21. A method according to claim 20, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

22. A method according to claim 1, wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

23. A method according to claim 1, wherein said analysis is performed by use of a single sensor.

24. The method according to claim 1, wherein said analyzing of said emission for the presence or absence of at least one predetermined volatile compound comprises obtaining a signature pattern of said predetermined volatile compound, wherein the signature pattern of said predetermined volatile compound is indicative of a disease state.

25. A method of diagnosing the presence of a causative agent of a particular disease state in a patient suffering from diarrhoea, the method comprising the steps of:
collecting a sample of an emission from the patient, wherein the emission is flatus or gas evolved from stool,
analysing the emission for the presence or absence of at least one predetermined volatile compound to obtain a result for said predetermined volatile compound that is indicative of the causative agent of a particular disease state, and
diagnosing the presence of said causative agent from said result.

26. A method according to claim 25, wherein the disease is acute.

27. A method according to claim 25, wherein the disease is an infection.

28. A method according to claim 27, wherein the infection is selected from the group consisting of *Clostridium difficle*, rotavirus, *Campylobacter* spp., adenovirus, astrovirus, and small round-structured virus.

29. A method according to claim 25, wherein the disease results from parasitic infestation.

30. A method according to claim 29, wherein the parasitic infestation is selected from the group consisting of infestation with *Giarda lamblia, Cryptospiridium* spp., *Leishmania* spp., *Schistoma* spp., *Onchocerca* and lola (filariasis).

31. A method according to claim 25, wherein the disease is chronic.

32. A method according to claim 31, wherein the disease is selected from the group consisting of Crohn's disease, Coeliac disease, ulcerative colitis, irritable bowel syndrome, inflammatory bowel disease, chronic pancreatitis, malabsorption syndrome, gastroenteritis, food intolerance and cancer.

33. A method according to claim 25, wherein the emission is collected non-invasively.

34. A method according to claim 25, wherein the emission is analysed by at least one of mass spectroscopy, gas chromatography electronic nose.

35. A method according to claim 25 wherein the predetermined volatile compound is selected from the group consisting of furans, ammonia, amines, acids, carboxylic acids, esters, ethers, alcohols, sulfides, sulphates, thiols, aldehydes, ketones, alkanes, alkenes, terpenes, phenols, indoles, nitrates, aromatic compounds, hydrocarbons and sugars.

36. A method according to claim 25, wherein said analysis is performed by use of a single sensor.

37. A method of analysing fluid emissions from a body to diagnose a disease state in said body, the method comprising the steps of:
collecting a sample of fluid emission from a body wherein the emission is flatus or gas evolved from a stool, and determining the absence of a predetermined volatile compound in said emission, wherein the absence of said predetermined volatile compound is indicative of a disease states
to diagnose said disease state in said body.

38. A method of diagnosing the presence of a causative agent of a particular disease state in a patient suffering from diarrhoea, the method comprising the steps of:
collecting a sample of an emission from the patient, wherein the emission is flatus or gas evolved from stool,
analysing the emission for the absence of at least one predetermined volatile compound to obtain a result for said predetermined volatile compound that is indicative of the causative agent of a particular disease state, and
diagnosing the presence of said causative agent from said result.

* * * * *

UNITED STATES PATENT AND TRADEMARK OFFICE
CERTIFICATE OF CORRECTION

PATENT NO. : 7,306,953 B2  Page 1 of 1
APPLICATION NO. : 11/036206
DATED : December 11, 2007
INVENTOR(S) : Christopher Simon J. Probert It is certified that error appears in the above-identified patent and that said Letters Patent is hereby corrected as shown below:

text:
In Column 14, line 14, delete the word "lola" and replace with the following --Iola--

In Column 14, line 27, following "chromatography", insert the following text:
--and-- text:
In Column 14, line 45, delete the word "states" and replace with the following --state--

Signed and Sealed this

Tenth Day of March, 2009

JOHN DOLL
*Acting Director of the United States Patent and Trademark Office*